United States Patent [19]

Berg

[11] Patent Number: 4,514,262

[45] Date of Patent: * Apr. 30, 1985

[54] SEPARATION OF BENZENE FROM NON-AROMATIC HYDROCARBONS BY EXTRACTIVE DISTILLATION

[76] Inventor: Lloyd Berg, 1314 S. Third Ave., Bozeman, Mont. 59715

[*] Notice: The portion of the term of this patent subsequent to Dec. 14, 1999 has been disclaimed.

[21] Appl. No.: 404,448

[22] Filed: Aug. 2, 1982

[51] Int. Cl.³ .......................... B01D 3/40; C07C 7/08
[52] U.S. Cl. ...................................... 203/51; 203/56; 203/57; 203/58; 203/60; 203/61; 203/62; 203/63; 203/64; 203/65; 585/864; 585/866
[58] Field of Search ...................... 203/56, 61, 51, 57, 203/58, 60, 62, 63, 64, 65; 585/833, 864, 866, 867, 856, 800, 855, 804, 807, 808, 857, 865, 860

[56] References Cited

U.S. PATENT DOCUMENTS

| | | | |
|---|---|---|---|
| 2,655,467 | 10/1953 | Cooper et al. | 203/61 |
| 2,842,484 | 7/1958 | Fleck | 203/56 |
| 3,869,377 | 3/1975 | Eisenlohr et al. | 585/865 |
| 3,882,013 | 5/1975 | Katsobashvili et al. | 585/319 |
| 3,884,769 | 5/1975 | Mikitenko et al. | 203/53 |
| 3,996,305 | 12/1976 | Berger | 585/470 |
| 4,041,091 | 8/1977 | Henry | 203/25 |
| 4,363,704 | 12/1982 | Berg | 203/61 |

Primary Examiner—Wilbur Bascomb

[57] ABSTRACT

Benzene is virtually impossible to separate from similar close boiling non-aromatic hydrocarbons by conventional rectification or distillation. Benzene can be readily separated from similar boiling non-aromatic hydrocarbons by using extractive distillation in which the extractive agent is a mixture of benzoic acid, maleic anhydride and/or phthalic anhydride plus a suitable solvent. A typical mixture comprises phthalic anhydride, maleic anhydride and adiponitrile.

5 Claims, No Drawings

SEPARATION OF BENZENE FROM NON-AROMATIC HYDROCARBONS BY EXTRACTIVE DISTILLATION

FIELD OF THE INVENTION

This invention relates to a method for separating benzene from close boiling non-aromatic hydrocarbons using mixtures of two or more compounds as extractive agents in extractive distillation.

DESCRIPTION OF THE PRIOR ART

Extractive distillation is the method of separating close boiling compounds by carrying out the distillation in a multi-plate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum boiling azeotropes with them. Usually the extractive agent is introduced a few plates from the top of the column to insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another recification column, cooling and phase separation, or solvent extraction.

The operation of an extractive distillation system has been well described by Butler, U.S. Pat. No. 3,114,783. He suggests a large number of pure compounds including alcohols, glycol ethers and sulfolanes to separate both benzene and toluene. No information is given here on the relative volatility and thus relative performance of these compounds as extractive distillation agents. Atlani et al, French Pat. No. 2,335,584, July 15, 1977 describes the use of several cyanamide derivatives as extractive agents for separating aromatics including benzene from naphthenes and dienes. Cooper, U.S. Pat. No. 2,655,467 employs molten phthalic anhydride as the extractive distillation agent to separate aromatics including benzene from non-aromatic hydrocarbons. P. Mikitinko, G. Cohen & L. Asselinieau, German Pat. No. 2,313,603, Sept. 27, 1973, separated both benzene and toluene from non-aromatic hydrocarbons using dimethyl formamide and dimethyl acetamide. P. Mikitinko & L. Asselinieau in German Pat. No. 2,809,985, Sept 14, 1978, use these same reagents with water added to bring the non-aromatic hydrocarbons off overhead as a two-phase azeotrope and thus lower the boiling point. E. Eisenlohr & H. Mueller in German Pat. No. 2,263,344, Dec. 23, 1972 reported on an improved equipment arrangement to separate both benzene and toluene from non-aromatic hydrocarbons by extractive distillation. G. Preusser, M. Schulze, K. Richter & W. Heuwels in German Pat. No. 1,960,857, Dec. 4, 1969 described the use of morpholine and some of its derivatives for this separation. Improved equipment for this separation was presented by E. Mueller & K. P. John in German Pat. No. 1,808,758, Nov. 14, 1968. It should be noted that all the work reported to date deals with the use of a single compound as the extractive distillation agent.

The advantage of using extractive distillation in this separation can be seen from Table I below.

TABLE I

Theoretical and Actual Plates Required vs. Relative Volatility for Benzene-Cyclohexane Separation.

| Relative Volatility | Theoretical Plates Required at Total Reflux, 99.9% Purity | Actual Plates Required, 75% Eff. |
|---|---|---|
| 1.02 | 750 | 1000 |
| 1.25 | 100 | 133 |
| 1.5 | 34 | 45 |
| 2.0 | 20 | 27 |
| 2.5 | 15 | 20 |
| 3.0 | 13 | 17 |
| 3.5 | 11 | 15 |
| 4.0 | 10 | 13 |
| 4.5 | 9 | 12 |

The relative volatility of benzene to cyclohexane is about 1.02. To separate these two by conventional rectification requires a minimum of 750 theoretical plates. This however is at total reflux. At a specific reflux, it will be more. The theoretical plates have to be converted to actual plates. Plate efficiencies of 75% are commonly employed and this is the basis of the actual plate listing in Table I. Thus more than 1000 actual plates are required, clearly an impossible separation. Several extractive distillation agents that I have discovered push the relative volatility as high as 4.5 and Table I shows that they will reduce the actual plate requirement to something close to 12 plates. Converting from total reflux to an actual reflux will increase the plate requirement somewhat but still make for a very attractive separation.

Extractive distillation typically requires the addition of an equal amount to twice as much extractive agent as close boiling compounds on each plate of the rectification column. The extractive distillation agent should be heated to about the same temperature as the plate into which it is introduced. Thus extractive distillation imposes an additional heat requirement on the column as well as somewhat larger plates for the same product output. To be economically attractive, the extractive distillation system must save more in the reduction of the number of theoretical plates and the size of the column than it adds in the cost of larger plates and the additional heat requirement. This will vary depending on the difficulty of the separation and the cost of heat. I found that in the separation of benzene from cyclohexane, the extractive agent should increase the relative volatility to about 1.5 to make the proccess economically attractive under the equipment and heat costs in effect at the time of my investigation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. I recommend twenty Centigrade degrees or more difference.

Benzene is the major precursor to many processes for making plastics and dyes. In these uses it is absolutely essential that the benzene be very pure. It is the presence of impurities that make it a poor polymerizing agent as a plastic or render it inconsistent as a dye intermediate. More than half of the benzene of commerce originates in or is converted from petroleum. From this source it is always accompanied by close boiling non-aromatic hydrocarbons of the paraffin, olefin and/or naphthene family.

OBJECTIVE OF THE INVENTION

The object of this invention is to provide a process or method of extractive distillation that will enhance the apparent relative volatility of benzene to close boiling non-aromatic hydrocarbons in their separation in a rectification column. It is a particular object of this invention to identify suitable mixtures of organic compounds which will increase the apparent relative volatility of benzene to close boiling non-aromatic hydrocarbons to values higher than that attained by single compounds. It is a further object of this invention to identify mixtures of organic compounds which, in addition to the above constraints, are stable, can be separated from the benzene by rectification with relatively few actual plates and can be recycled to the extractive distillation column and reused with little decomposition.

SUMMARY OF THE INVENTION

The objects of this invention are provided by a process for the separation of benzene from close boiling non-aromatic hydrocarbons using mixtures of benzoic acid, maleic anhydride, phthalic anhydride and/or an oxygenated or nitrogen-containing organic compound as the agent in extractive distillation.

DETAILED DESCRIPTION OF THE INVENTION

I have discovered that a mixture comprising an organic compound admixed with benxoic acid, maleic anhydride, phthalic anhydride and/or two of these, is more effective as an extractive distillation agent in the separation of benzene from close boiling non-aromatic hydrocarbons than the compounds when used alone. In order to demonstrate this invention, I evaluated extractive agents with benzene (b.p.=80.1° C.)-cyclohexane (b.p.=80.8° C., a naphthene) and with benzene-2,4-dimethylpentane (b.p.=80.6° C., a paraffin). The relatively volatility of benzene to cyclohexane is 1.02, to 2,4-dimethylpentane it is 1.01.

Table II shows the relative volatility of benzene to cyclohexane and benzene to 2,4-diemthylpentane with a number of solvents mixed with phthalic anhydride, maleic anhydride or both. Table III shows the relative volatility of benzene to cyclohexane and benzene to 2,4-dimethylpentane with a number of solvents mixed with benzoic acid, maleic anhydride or both. All of the systems in Tables II and III possess a relative volatility of 2.5 or greater. Table IV shows a number systems involving phthalic anhydride, maleic anhydride, benzoic acid and/or a solvent possessing a relative volatility in the range of 1.5 to 2.5. The relative volatilities shown in Tables II, III and IV are the average of two runs, one at one part of extractive agent per part of hydrocarbon mixture and the other at 6/5 parts of extractive agent per part of hydrocarbon mixture. I have found that this is the preferred ratio of extractive distillation agent to hydrocarbon in this separation. The amount of phthalic anhydride, maleic anhydride, benzoic acid and solvent in the ternarys shown in Tables II, III and IV was approximately equal to each other as were the binarys also. The exact ratio does not appear to be critical. Likewise the relative volatilities shown in Tables II, III and IV do not change appreciably when the ratio of benzene to non-aromatic hydrocarbon is varied. The data presented in Tables II, III and IV were obtained in a glass vapor-liquid equilibrium still of the Othmer design.

THE USEFULNESS OF THE INVENTION

The usefulness or utility of this invention can be demonstrated by referring to the data presented in Tables I, II and III. When benzene is being separated from cyclohexane, relative volatility=1.02, by rectification in 99.9% purity, Table I shows that more than 1000 acutal plates are required. Table II shows that a mixture of phthalic anhydride, maleic anhydride and adiponitrile changes the relative volatility to 4.07 and referring to Table I, this requires only a little more than ten actual plates. Table II also shows that this mixture will change the relative volatility of benzene-2,4-dimethylpentane to 4.44.

TABLE II

Relative Volatilities of Benzene and Cyclohexane or 2,4-Dimethylpentane with Mixtures of Phthalic anhydride Maleic Anhydride and/or a Solvent

| Extractive Distillation Agent | Cyclohexane-Benzene | 2,4-TriMeC$_5$—Benzene |
| --- | --- | --- |
| Ph. anh., Mal. anh., Phenol | 2.51 | 4.12 |
| Ph. anh., Phenol | 2.28 | |
| Mal. anh., Phenol | 2.52 | |
| Phenol | 2.01 | |
| Ph. anh., Mal. anh., Dimethylformamide | 3.04 | 3.36 |
| Ph. anh., Dimethylformamide | 2.35 | |
| Mal. anh., Dimethylformamide | 2.67 | |
| Dimethylformamide | 2.03 | |
| Ph. anh., Mal. anh., Dimethylsulfoxide | 3.73 | 4.03 |
| Ph. anh., Dimethylsulfoxide | 3.67 | |
| Mal. anh., Dimethylsulfoxide | 3.86 | |
| Dimethylsulfoxide | 2.65 | |
| Ph. anh., Mal. anh., 2,4-Pentanedione | 2.67 | 4.25 |
| Ph. anh., 2,4-Pentanedione | 2.31 | |
| Mal. anh., 2,4-Pentanedione | 2.51 | |
| 2,4-Pentanedione | 2.93 | |
| Ph. anh., Mel. anh., Ethylene glycol phenyl ether | 3.13 | 3.27 |
| Ph. anh., Ethylene glycol phenyl ether | 2.38 | |
| Mal. anh., Ethylene glycol phenyl ether | 2.66 | |

TABLE II-continued

Relative Volatilities of Benzene and Cyclohexane or 2,4-Dimethylpentane with Mixtures of Phthalic anhydride Maleic Anhydride and/or a Solvent

| Extractive Distillation Agent | Cyclohexane-Benzene | 2,4-TriMeC$_5$-Benzene |
|---|---|---|
| Ethylene glycol phenyl ether | 2.22 | |
| Ph. anh., Mal. anh., Nitrobenzene | 2.83 | 3.05 |
| Ph. anh., Nitrobenzene | Will not dissolve | |
| Mal. anh., Nitrobenzene | 3.07 | |
| Nitrobenzene | 2.15 | |
| Ph. anh., Mal. anh., Benzophenone | 2.98 | 3.45 |
| Ph. anh., Benzophenone | Will not dissolve | |
| Mal. anh., Benzophenone | 2.98 | |
| Benzophenone | 2.68 | |
| Ph. anh., Mal. anh., Furfural | 3.00 | 4.58 |
| Ph. anh., Furfural | 2.80 | |
| Mal. anh., Furfural | 3.09 | |
| Furfural | 2.50 | |
| Ph. anh., Mal. anh., 1-Me—2-pyrrolidinone | 4.21 | 4.01 |
| Ph. anh., 1-Me—2-pyrrolidinone | 4.18 | |
| Mal. anh., 1-Me—2-pyrrolidinone | 3.46 | |
| 1-Me—2-pyrrolidinone | 2.51 | |
| Ph. anh., Mal. anh., Sulfolane | 3.55 | 5.66 |
| Ph. anh., Sulfolane | 2.83 | |
| Mal. anh., Sulfolane | 2.84 | |
| Sulfolane | 3.43 | |
| Ph. anh. Mal. anh., N,N—diMe acetamide | 3.43 | 4.13 |
| Ph. anh., N,N—diMe acetamide | 2.66 | |
| Mal. anh., N,N—diMe acetamide | 3.31 | |
| N,N—diMe acetamide | 3.07 | |
| Ph. anh., Mal. anh., Glycerol triacetate | 3.15 | 4.41 |
| Ph. anh., Glycerol triacetate | Will not dissolve | |
| Mal. anh., Glycerol triacetate | 3.35 | |
| Glycerol triacetate | 2.20 | |
| Ph. anh., Mal. anh., Acetophenone | 2.52 | 3.57 |
| Ph. anh., Acetophenone | 2.48 | |
| Mal. anh., Acetophenone | 2.70 | |
| Acetophenone | 1.92 | |
| Ph. anh., Mal. anh., Ethylacetoacetate | 2.54 | 2.54 |
| Ph. anh., Ethylacetoacetate | 2.16 | |
| Mal. anh., Ethylacetoacetate | 2.69 | |
| Ethylacetoacetate | 1.94 | |
| Ph. anh., Mal. anh., N—IsoPr—2-pyrrolidone | 2.35 | |
| Ph. anh., N—IsoPr—2-pyrrolidone | 2.20 | |
| Mal. anh., N—IsoPr—2-pyrrolidone | 2.06 | |
| N—IsoPr—2-pyrrolidone | 1.81 | |
| Ph. anh., Mal. anh., Sulfolene | 3.15 | 6.16 |
| Ph. anh., Sulfolene | 3.18 | |
| Mal. anh., Sulfolene | 3.15 | |
| Sulfolene | 2.93 | |
| Ph. anh., Mel. anh., DiMeSulfone | 3.24 | |
| Ph. anh., DiMeSulfone | Will not dissolve | |
| Mal. anh., DiMeSulfone | Decomposes | |
| DiMeSulfone | Will not dissolve | |
| Ph. anh., Mal. anh., 2-Nitrotoluene | 2.81 | 3.16 |
| Ph. anh., 2-Nitrotoluene | 2.29 | |
| Mal. anh., 2-Nitrotoluene | 2.82 | |
| 2-Nitrotoluene | 2.13 | |
| Ph. anh., Mal. anh., Isobornyl acetate | 2.97 | |
| Ph. anh., Isobornyl acetate | Will not dissolve | |
| Mal. anh., Isobornyl acetate | 1.78 | |
| Isobornyl acetate | 1.27 | |
| Ph. anh., Mal. anh., Adiponitrile | 4.07 | 4.44 |
| Ph. anh., Adiponitrile | 3.84 | |
| Mal. anh., Adiponitrile | 3.68 | |
| Adiponitrile | 3.27 | |
| Ph. anh., Mal. anh., BuBenzyl phthalate | 3.18 | 4.66 |
| Ph. anh., BuBenzyl phthalate | Will not dissolve | |
| Mal. anh., BuBenzyl phthalate | 2.22 | |
| BuBenzyl phthalate | 2.44 | |
| Ph. anh., Mal .anh., Benzyl acetate | 2.96 | 3.90 |
| Ph. anh., Benzyl acetate | 1.59 | |
| Mal. anh., Benzyl acetate | 2.40 | |
| Benzyl acetate | 2.10 | |
| Ph. anh., Mal. anh., Diethyl oxalate | 2.87 | |
| Ph. anh., Mal. anh., Phenyl acetate | 2.64 | |
| Ph. anh, Mal. anh., Dipropylene glycol | 2.85 | |
| Ph. anh., Mal. anh., Butoxypropanol | 2.73 | |
| Ph. anh., Mal. anh., Phenylacetic acid | 2.67 | |
| Ph. anh., Mal. anh., Anisole | 2.67 | |

TABLE III

Relative Volatilities of Benzene and Cyclohexane or 2,4-Dimethylpentane with Mixtures of Benzoic Acid, Maleic Anhydride and/or a Solvent.

| Extractive Distillation Agent | Cyclohexane Benzene | 2,4-TriMePentane Benzene |
|---|---|---|
| Benz. acid, Mal. anh., 3-Sulfolene | 3.71 | 5.55 |
| Benz. acid, 3-Sulfolene | 3.35 | |
| Mal. anh., 3-Sulfolene | 3.15 | |
| 3-Sulfolene | 3.22 | |
| Benz. acid, Mal. anh., Dimethylsulfone | 3.10 | 4.21 |
| Benz. acid, Dimethylsulfone | Will not dissolve | |
| Mal. anh., Dimethylsulfone | Decomposes | |
| Dimethylsulfone | Will not dissolve | |
| Benz. acid, Mal. anh., Sulfolane | 3.06 | 3.94 |
| Benz. acid, Sulfolane | 2.90 | |
| Mal. anh., Sulfolane | 2.84 | |
| Sulfolane | 3.42 | |
| Benz. acid, Mal. anh., Adiponitrile | 3.17 | 4.01 |
| Benz. acid, Adiponitrile | 1.81 | |
| Mal. anh., Adiponitrile | 3.68 | |
| Adiponitrile | 3.27 | |
| Benz. acid, Mal. anh., 1-Me—2-pyrrolidinone | 2.76 | 3.71 |
| Benz. acid, 1-Me—2-pyrrolidinone | 2.24 | |
| Mal. anh., 1-Me—2-pyrrolidinone | 3.46 | |
| 1-Me—2-pyrrolidinone | 2.51 | |
| Benz. acid, Mal. anh., N,N—diMe acetamide | 4.21 | 3.30 |
| Benz. acid, N,N—diMe acetamide | 2.07 | |
| Mal. anh., N,N—diMe acetamide | 3.31 | |
| N,N—diMe acetamide | 3.08 | |
| Benz. acid, Mal. anh., Nitrobenzene | 2.97 | 3.62 |
| Benz. acid, Nitrobenzene | 2.12 | |
| Mal. anh., Nitrobenzene | 3.07 | |
| Nitrobenzene | 2.15 | |
| Benz. acid, Mal. anh., Triethylene glycol diacetate | 2.51 | 3.82 |
| Benz. acid, Triethylene glycol diacetate | 1.52 | |
| Mal. anh., Triethylene glycol diacetate | 2.17 | |
| Triethylene glycol diacetate | 2.07 | |
| Benz. acid, Mal. anh., Dimethylformamide | 2.67 | |
| Benz. acid, Mal. anh., Formamide | 3.83 | 2.22 |
| Benz. acid, Formamide | 3.35 | |
| Mal. anh., Formamide | 1.71 | |
| Formamide | 1.25 | |

TABLE IV

Relative Volatilities of Benzene and Cyclohexane with Several Solvent Mixtures.

| Extractive Distillation Agent | Cyclohexane-Benzene |
|---|---|
| Ph. anh., Mal. anh., N(N,N—diMe aminopropyl)-2-pyrrolidone | 1.48 |
| Ph. anh., Mal. anh., Tetrahydrofurfuryl alcohol | 2.38 |
| N(N,N—diMe aminopropyl)-2-pyrrolidone | 2.18 |
| Ph. anh., Mal. anh., Diethyl maleate | 2.45 |
| Ph. anh., Mal. anh., Isophorone | 2.42 |
| Ph. anh., Mal. anh., Methylbenzoate | 2.46 |
| Ph. anh., Mal. anh., Diethylene glycol | 1.60 |
| Ph. anh., Mal. anh., n-Octanol | 2.39 |
| Benz. acid, Mal. anh., 2-Nitrotoluene | 2.28 |
| Benz. acid, Mal. anh., Furfural | 1.78 |
| Benz. acid, Mal. anh., Ethylene glycol diacetate | 2.33 |
| Benz. acid, Mal. anh., Phenol | 2.22 |
| Benz. acid, Mal. anh., 3-Nitrotoluene | 1.80 |
| Benz. acid, Mal. anh., Acetophenone | 1.75 |
| Benz. acid., Mal. anh., Ethylene glycol phenyl ether | 2.06 |

These are the naphthene and paraffin boiling closest to benzene and therefore all other hydrocarbons will be easier to separate than either of these two. Thus extractive distillation by rectification in columns of ten to twelve actual plates will easily separate benzene from any other hyrdocarbon.

WORKING EXAMPLES

Example 1

A mixture comprising 50 grams of benzene and 50 grams of cyclohexane was charged to an Othmer type vapor-liquid equilibrium still and the mixture refluxed for seven hours. Samples of the vapor and liquid were removed and analysed by gas chromatography. The vapor contained 40.1% benzene, 59.9% cyclohexane, the liquid 39.8% benzene, 60.2% cyclohexane. This indicates a relative volatility of cyclohexane to benzene of 1.02. This has been confirmed by other investigators.

Example 2

A mixture comprising 35 grams of benzene and 65 grams of 2,4-dimethylpentane was charged to the vapor-liquid equilibrium still and refluxed for six hours. Analysis indicated a vapor composition of 35.5% benzene, 64.5% 2,4-dimethylpentane and a liquid of 35.2% benzene and 64.8% 2,4-dimethylpentane. This indicates a relative volatility of 1.01.

Example 3

A mixture comprising 25 grams benzene, 25 grams cyclohexane and 50 grams of adiponitrile was charged to the vapor-liquid equilibrium still and refluxed for twelve hours. Analysis gave a vapor composition of 73.7% cyclohexane, 26.3% benzene and a liquid composition of 43.1% cyclohexane, 56.9% benzene. This indicates a relative volatility of 3.67. Ten grams of adiponitrile were added and refluxing continued for another eleven hours. Analysis gave a vapor composition of 76.8% cyclohexane, 23.2% benzene and a liquid composition of 53.6% cyclohexane, 46.4% benzene. This indicates a relative volatility of 2.87.

Example 4

A mixture comprising 25 grams benzene, 25 grams cyclohexane, 25 grams maleic anhydride and 25 grams adiponitrile was charged to the vapor-liquid equilibrium still and refluxed for twelve hours. Analysis gave a vapor composition of 80.5% cyclohexane, 19.5% benzene and a liquid composition of 56% cyclohexane, 44% benzene. This indicates a relative volatility of 3.25. Five grams of maleic anhydride and 5 grams of adiponitrile were added and refluxing continued for another 13 hours. Analysis gave a vapor composition of 80.4% cyclohexane, 19.6% benzene and a liquid composition of 50% cyclohexane, 50% benzene. This indicates a relative volatility of 4.10.

Example 5

A mixture comprising 25 grams benzene, 25 grams cyclohexane, 25 grams phthalic anhydride and 25 grams adiponitrile was charged to the vapor-liquid equilibrium still and refluxed for thirteen hours. Analysis gave a vapor composition of 80% cyclohexane, 20% benzene and a liquid composition of 55.3% cyclohexane, 44.7% benzene. This indicates a relative volatility of 3.23. Two grams of phthalic anhydride and eight grams of adiponitrile were added and refluxing continued for another ten hours. Analysis gave a vapor composition of 87.5% cyclohexane, 12.5% benzene and a liquid composition of 60.9% cyclohexane, 39.1% benzene. This indicates a relative volatility of 4.45.

Example 6

A mixture comprising 25 grams benzene, 25 grams cyclohexane, 17 grams phthalic anhydride, 17 grams maleic anhydride and 17 grams adiponitrile was charged to the vapor-liquid equilibrium still and refluxed for 14 hours. Analysis gave a vapor composition of 73.6% cyclohexane, 26.4% benzene and a liquid composition of 37.9% cyclohexane, 62.1% benzene. This indicates a relative volatility of 4.57. Three grams each of phthalic anhydride, maleic anhydride and adiponitrile were added and refluxing continued for another ten hours. Analysis gave a vapor composition of 68.6% cyclohexane, 31.4% benzene and a liquid composition of 38% cyclohexane, 62% benzene. This indicates a relative volatility of 3.56.

Example 7

A mixture comprising 25 grams benzene, 25 grams 2,4-dimethylpentane, 17 grams phthalic anhydride, 17 grams maleic anhydride and 17 grams adiponitrile was charged to the vapor-liquid equilibrium still and refluxed for eleven hours. Analysis gave a vapor composition of 77.3% 2,4-dimethylpentane, 22.7% benzene and a liquid composition of 45.3% 2,4-dimethylpentane, 54.7% benzene. This indicates a relative volatility of 4.11. Three grams each of phthalic anhydride, maleic anhydride and adiponitrile were added and refluxing continued for another twelve hours. Analysis gave a vapor composition of 78.9% 2,4-dimethylpentane, 21.1% benzene and a liquid composition of 47.4% 2,4-dimethylpentane, 52.6% benzene. This indicates a relative volatility of 4.17.

These examples serve to show in detail how the data presented in Tables II, III and IV was obtained. Each of the solvent combinations reported there was determined in this manner.

Example 8

A column consisting of one ten-plate section of one-inch diameter glass perforated plates equipped with a vacuum jacket was employed. The column was fitted with a Corad constant reflux ratio distilling head. Between the Corad head and the top of the column, a feed line from a constant flow bellows pump was introduced. The column had been calibrated with a test mixture of ethylbenzene and p-xylene, which mixture possesses a relative volatility of 1.06. The column calibrated 4.5 theoretical plates at total reflux. A run was made with a charge comprising approximately 10% cyclohexane, 90% benzene in the stillpot. The column was operated at total reflux for about an hour and then the pump started at a rate to deliver about one part of extractive agent to one part of cyclohexane-benzene being boiled up. The extractive agent in this example was 33.3% phthalic anhydride, 33.3% maleic anhydride and 33.3% adiponitrile. The following data were obtained:

| Time, hours | Overhead Composition, | | Stillpot Composition, | | Relative Volatility |
|---|---|---|---|---|---|
| | % CH, | % Benz. | % CH, | % Benz. | |
| 1 | 90.7 | 9.3 | 7 | 93 | 2.93 |
| 2 | 96.1 | 3.9 | 4.9 | 95.1 | 3.92 |
| 3 | 96.2 | 3.8 | 4.2 | 95.8 | 4.09 |

It will be noted that after about two hours, equilibrium has been achieved and the relative volatility remains essentially constant in the range of 3.9 to 4.1. Without the extractive agent it would have been 1.02.

I have shown by experimental data and examples that the proper combination of benzoic acid, maleic anhydride and/or phthalic anhydride with a suitable solvent will yield separations of benzene from close boiling non-aromatic hydrocarbons that are far better than what is obtainable by any of these compounds individually. The total effect of the mixture far exceeds the sum of the parts.

The nature of the present invention having been described and illustrated by examples, what I wish to claim as new and useful and secure by Letters Patent is:

1. A method for separating benzene from close boiling non-aromatic hydrocarbons which comprises distilling a mixture of benzene and close boiling non-aromatic hydrocarbons in a rectification column in the presence of a sufficient amount of an extractive agent to provide a relative volatility of 2.0 or greater comprising effective proportions of at least phthalic anhydride and at least one solvent from the group consisting of acetophenone, adiponitrile, anisole, benzophenone, benzyl acetate, butoxypropanol, butyl benzyl phthalate, diethyl maleate, diethyl oxalate, diethylene glycol, N,N-dimethyl acetamide, N(N,N-dimethylaminopropyl)-2-pyrrolidine, dimethylformamide, dimethylsulfone, dimethylsulfoxide, dipropylene glycol, ethyl acetoacetate, ethylene glycol diacetate, ethylene glycol phenyl ether, formamide, furfural, glycerol triacetate, isobornyl acetate, isophorone, N-isopropyl-2-pyrrolidone, 1-methyl-2-pyrrolidinone, nitrobenzene, 2-nitrotoluene, 3-nitrotoluene, n-octanol, 2,4-pentanedione, phenol, phenyl acetate, phenyl acetic acid, sulfolane, sulfolene, tetrahydrofurfuryl alcohol, and triethylene glycol diacetate.

2. The method of claim 1 in which the extractive agent comprises phthalic anhydride, maleic anhydride and a at least one of said solvents.

3. A method for separating benzene from close boiling non-aromatic hydrocarbons which comprises distilling a mixture of benzene and close boiling non-aromatic hydrocarbons in a rectification column in the presence of a sufficient amount of an extractive agent to provide a relative volatility of 2.0 or greater comprising effective proportions of at least benzoic acid and at least one solvent from the group consisting of adiponitrile, N,N-dimethylacetamide, dimethylformamide, dimethylsulfone, formamide, 1-methyl-2-pyrrolidinone, nitrobenzene, sulfolane, 3-sulfolene, and triethylene-glycol diacetate.

4. The method of claim 3 in which the extractive agent comprises benzoic acid, maleic anhydride and one of said solvents .

5. A method for separating benzene from close boiling non-aromatic hydrocarbons which comprises distilling a mixture of benzene and close boiling non-aromatic hydrocarbons in a rectification column in the presence of a sufficient amount of an extractive agent to provide a relative volatility of 2.0 or greater comprising effective proportions of maleic anhydride and at least one solvent from the group consisting of acetophenone, adiponitrile, anisole, benzophenone, benzyl acetate, butoxypropanol, butyl benzyl phthalate, diethyl maleate, diethyl oxalate, diethylene glycol, N,N-dimethyl acetamide, N(N,N-dimethylaminopropyl)-2-pyrrolidine, dimethylformamide, dimethylsulfone, dimethylsulfoxide, dipropylene glycol, ethyl acetoacetate, ethylene glycol diacetate, ethylene glycol phenyl ether, formamide, furfural, glycerol triacetate, isobornyl acetate, isophorone, N-isopropyl-2-pyrrolidone, 1-methyl-2-pyrrolidinone, nitrobenzene, 2-nitrotoluene, 3-nitrotoluene, n-octanol, 2,4-pentanedione, phenol, phenyl acetate, phenyl acetic acid, sulfolane, sulfolene, tetrahydorfurfuryl alcohol and triethylene glycol diacetate.

* * * * *